(12) United States Patent
Rynhart et al.

(10) Patent No.: US 6,340,892 B1
(45) Date of Patent: Jan. 22, 2002

(54) HAND-HELD DIGITAL MOISTURE METER WITH MEMORY AND COMMUNICATIONS

(75) Inventors: Alan Rynhart, Co. Wicklow; John Fallon, Dublin; James McIlroy, Dublin; Dominic Southgate, Dublin, all of (IE)

(73) Assignee: Rynhart Research Limited, Delgany (IE)

( * ) Notice: Subject to any disclaimer, the term of this patent is extended or adjusted under 35 U.S.C. 154(b) by 0 days.

(21) Appl. No.: 09/511,326

(22) Filed: Feb. 23, 2000

(30) Foreign Application Priority Data

Feb. 23, 1999 (IE) ................................. 990146
Mar. 5, 1999 (IE) ................................. 990188

(51) Int. Cl.[7] ............................................. G01R 27/32
(52) U.S. Cl. .................... 324/640; 324/664; 702/104
(58) Field of Search ................... 324/664, 669, 324/670, 640; 73/73; 702/100, 104, 50, 52, 55, 30

(56) References Cited

U.S. PATENT DOCUMENTS

| | | | | | |
|---|---|---|---|---|---|
| 4,399,404 | A | * | 8/1983 | Resh | 324/689 |
| 4,580,233 | A | * | 4/1986 | Parker et al. | 73/73 |
| 4,588,943 | A | * | 5/1986 | Hirth | 324/664 |
| 5,621,391 | A | * | 4/1997 | Elseth | 340/604 |
| 5,621,669 | A | * | 4/1997 | Bjornsson | 702/85 |
| 5,994,908 | A | * | 11/1999 | McMahon | 324/694 |

* cited by examiner

Primary Examiner—Ernest Karlsen
Assistant Examiner—Russell M. Kobert
(74) Attorney, Agent, or Firm—Jacobson Holman, PLLC (57) ABSTRACT

A moisture meter (1) has an LCD display (8) driven by a digital microcontroller (50) which generates digital moisture reading data. Readings are stored as discrete records in files. The microcontroller (51) stores a library of material data and automatically compensates signals from a capacitive/impedance sensor circuit (51) according to both stored material parameter values and sensed temperature. Users may edit the parameter values. A non-removable cover (4) is used at the final stage of production to configure the meter for the nature of interfacing (such as serial port interfacing) required.

21 Claims, 10 Drawing Sheets

| No. | WOOD | |
|---|---|---|
| | SPECIES | SG |
| 1 | Ash Silvertop | .72 |
| 2 | Ash White Amr | .60 |
| 3 | Beech America | .64 |
| 4 | Birch Yellow | .62 |
| 5 | Cedar Red Wst | .33 |
| 6 | Cherry Black | .50 |
| 7 | Deal Red | .51 |
| 8 | Deal White | .47 |
| 9 | Elm Red | .54 |
| 10 | Fir Douglas | .50 |
| 11 | Hickory Pecan | .66 |
| 12 | Kiri | .32 |
| 13 | Mahogany Amer | .56 |
| 14 | Maple Black | .60 |
| 15 | Maple Red | .55 |
| 16 | Meranti L Red | .55 |
| 17 | Meranti White | .66 |
| 18 | Mesquite | .80 |
| 19 | Oak European | .70 |
| 20 | Oak Japanese | .66 |
| 21 | Oak Red North | .63 |
| 22 | Oak White Amr | .70 |
| 23 | Pine Longleaf | .60 |
| 24 | Pine Scotch | .50 |
| 25 | Pine White | .39 |
| 26 | Poplar | .45 |
| 27 | Redwood | .40 |
| 28. | Spruce Sitka | .40 |
| 29 | Teak | .58 |
| 30 | Walnut | .56 |
| 31 | Willow Black | .40 |
| 32 | Set User SG | .50 |

| WALL |
|---|
| MATERIAL |
| Plaster |
| Brick |
| Drywall |

| ROOF |
|---|
| MATERIAL |
| PVC |
| Mod. Bitumen |
| BUR |

HAND-HELD DIGITAL MOISTURE METER WITH MEMORY AND COMMUNICATIONS

INTRODUCTION

1. Field of the Invention

The invention relates to a moisture meter of the type for surveying applications in which the meter is hand-held and, in use, is held so that a sensor attached to it is in contact with the material being surveyed.

2. Prior Art Discussion

While such meters are generally quite accurate, they suffer from a lack of versatility because they are configured for only one type of material and calibration for variations of material is difficult for the user. Also, it is necessary for the user to note down on paper readings from the dial, which is time-consuming and difficult in some environments such as attic spaces.

Objects of the Invention

It is therefore an object of the invention to provide a moisture meter which may be used with a wide range of different materials.

Another object is to provide for capture of moisture information in a more simple manner.

A further object is to provide for more accurate determination of moisture content.

SUMMARY OF THE INVENTION

According to the invention there is provided a moisture meter comprising a hand-held housing supporting a moisture sensor of the type for contact with a material being surveyed, an output interface, and a controller comprising means for determining moisture content data according to signals from a moisture sensor drive circuit and for outputting said data at the output interface, wherein:

the meter further comprises a user input interface, the controller comprises means for selecting stored material parameter values in response to user inputs, and the controller comprises means for performing data processing with said selected parameter values to determine moisture content of a material in contact with the moisture sensor.

In one embodiment, the controller comprises an analogue to digital converter for conversion of analogue signals from the moisture sensor drive circuit.

In one embodiment, the controller comprises means for setting gain values for the moisture sensor drive circuit according to the selected material parameter values.

In one embodiment, the controller comprises means for setting gain values by setting gain switches connected to a filter/amplifier/detector stage of the moisture sensor drive circuit.

In another embodiment, the filter/amplifier/detector stage is connected to a logarithmic amplifier comprising means for linearizing the exponential form of a signal from said stage and providing an output signal to the controller.

In one embodiment, the meter further comprises a temperature sensor and the controller comprises means for performing compensation according to a sensed temperature value.

In one embodiment, the controller comprises an analogue to digital converter and comprises means for correcting the output of said converter according to sensed temperature.

In a further embodiment, the controller is connected to a memory storing a library of material types and associated parameter values.

In one embodiment, the input interface comprises a key dedicated to each of a plurality of material type groups.

In one embodiment, the groups include wood, wall, and roof material types.

In one embodiment, the input interface comprises a scroll key and the controller comprises means for scrolling through library items in response to said scroll key.

In one embodiment, the controller comprises means for storing each moisture reading.

In one embodiment, the controller comprises means for storing each moisture reading as a discrete record within one of a plurality of files.

In a further embodiment, the controller comprises means for automatically writing material type, date, and time data to each record.

In one embodiment, the controller comprises means for communicating with a host computer via a bidirectional port.

In one embodiment, the controller comprises means for downloading updated material parameter values from a host computer.

In one embodiment, the controller comprises means for uploading data records to a host computer.

In one embodiment, the controller comprises means for automatically writing a temperature value for a reading to the associated data record.

In one embodiment, the meter housing comprises a non-removable cover adjacent to a side edge of a circuit board contained within the housing.

In another embodiment, the cover has an aperture for access to an interfacing device of the meter.

In one embodiment, the cover is in a top side of the meter housing.

In one embodiment, the cover comprises a pair of opposed snap-fitting tabs engaging behind corresponding receivers in housing main body.

BRIEF DESCRIPTION OF THE DRAWINGS

The invention will be more clearly understood from the following description of some embodiments thereof, given by way of example only with reference to the accompanying drawings in which.

DESCRIPTION OF THE INVENTION

Referring to the drawings, a moisture meter 1 is illustrated. The meter 1 is for measuring moisture in a range of materials, in this embodiment wood, dry-wall, plaster, brick, roofing, and siding. It operates non-destructively by contacting the material with conductive rubber electrodes mounted on the base of the meter and performing electrical impedance measurements. However, the meter of the invention may use other types of sensors and associated circuits such as conductive probes for insertion into a material such as wood, a humidity probe, or a temperature probe.

In more detail, the meter 1 has a housing formed from rear and front mouldings 2 and 3 respectively. The mouldings 2 and 3 together define a generally rectangular opening in the top of the meter 1 and this is covered by a non-removable cover 4, described in more detail below.

Figures 1A, 1B:
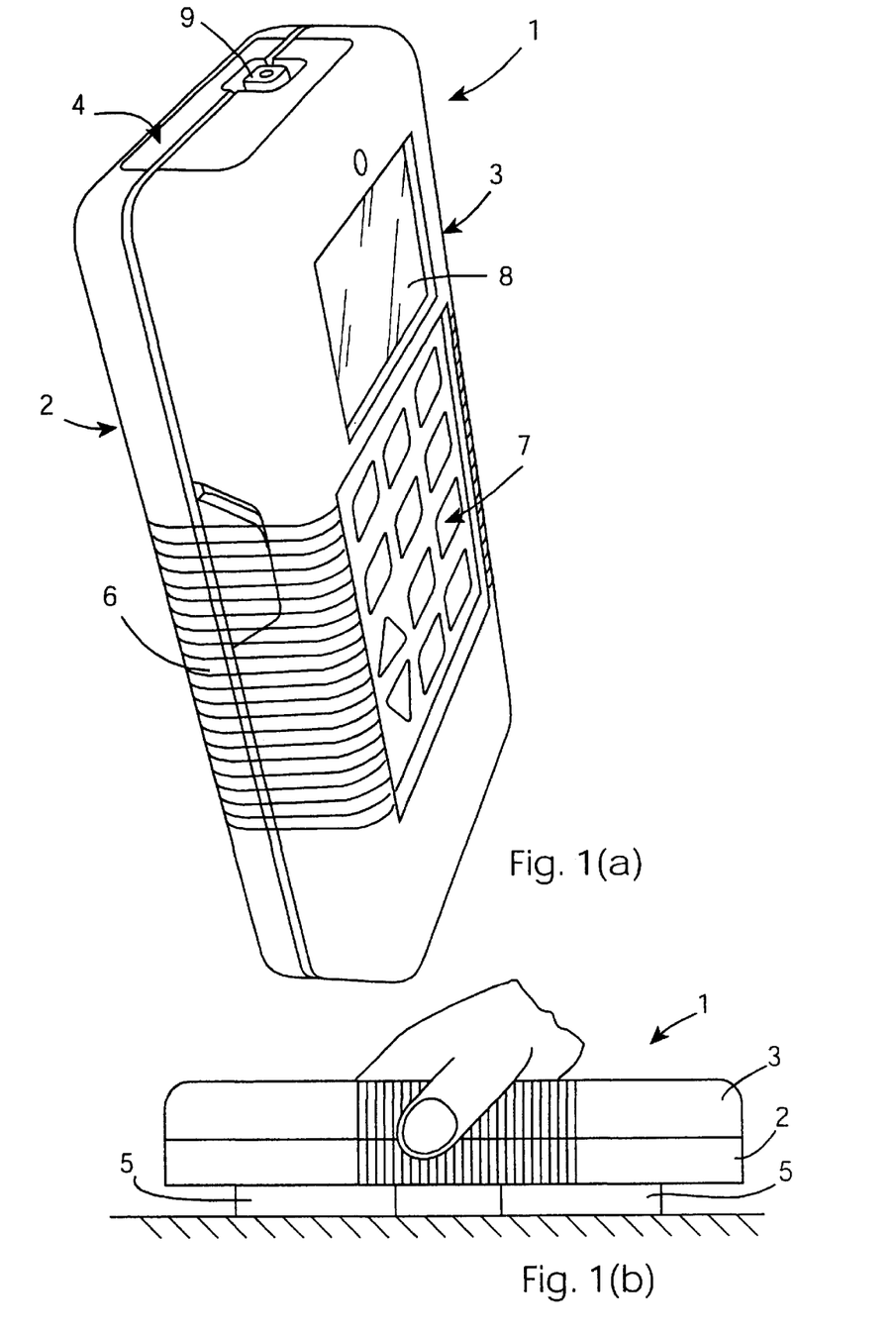
FIG. 1(a) is a perspective view from above of a moisture meter of the invention.
FIG. 1(b) is a diagrammatic side view showing the meter in use.

Conductive rubber electrodes 5 are mounted on the flat surface of the rear moulding 2, as shown in FIG. 1(b). The front moulding 3 has a pair of ribbed grips 6 and supports a keypad 7 and an LCD display 8. The cover 4 has an aperture which allows access to a communication socket 9.

The rear and front mouldings 2 and 3 are common across a range of variants of the meter 1, however each variant has an associated version of the cover 4.

Figure 2:
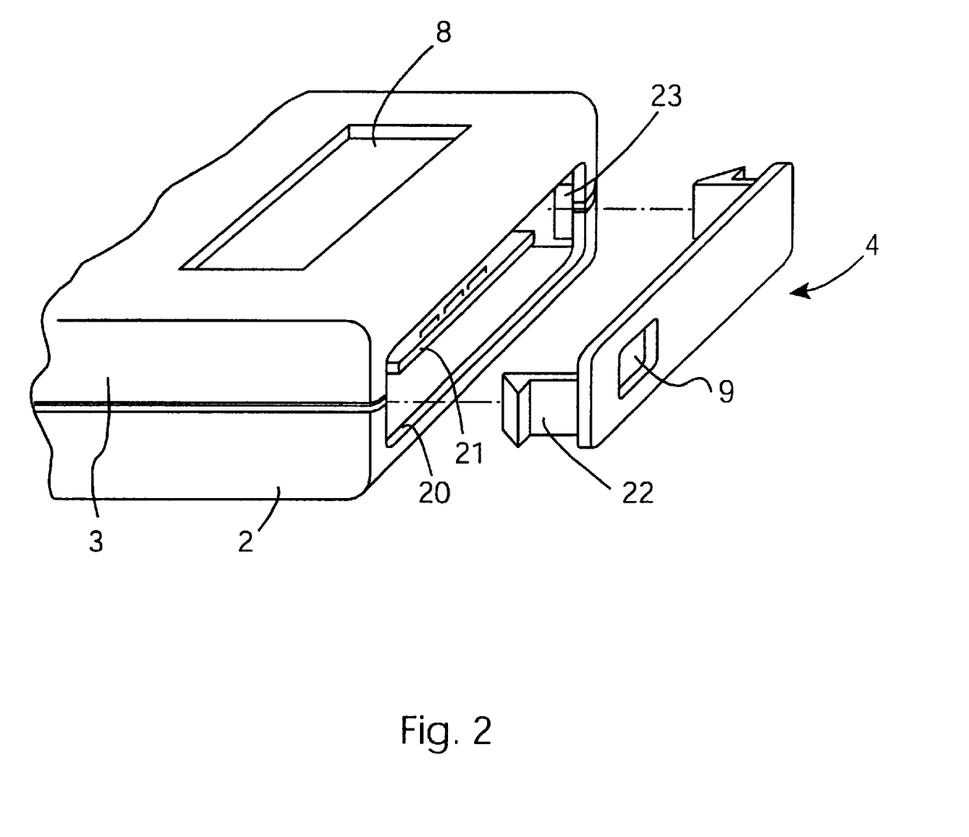
FIG. 2 is a perspective views of a cover of a housing of the meter.

As shown in FIG. 2, the cover 4 comprises tabs 22 which snap-fit behind receivers 23 of the mouldings 2 and 3 in a non-removable manner. The socket 9 comprises an aperture in the cover 4 in registry with a socket component on a circuit board 21 within the housing.

Choice of an appropriate cover allows the same mouldings 2 and 3 to be used because each cover has an appropriate interfacing aperture or device. A cover 30 shown in FIG. 3 has a blank cover portion 31. A cover 35 shown in FIG. 4 has a cover portion 36 comprising an aperture 37 to accommodate an RS232 mini din socket, and a sliding on/off switch 38. A cover 40 shown in FIG. 5 comprises a cover portion 41 with a rocker on/off switch 42. Another type of cover may include an aperture for a lead connecting a circuit to a probe, for example. The cover is pushed into position at the end of the production process, and up to then there is access to the circuit board 21 for operations such as calibration with a potentiometer.

Figure 3:
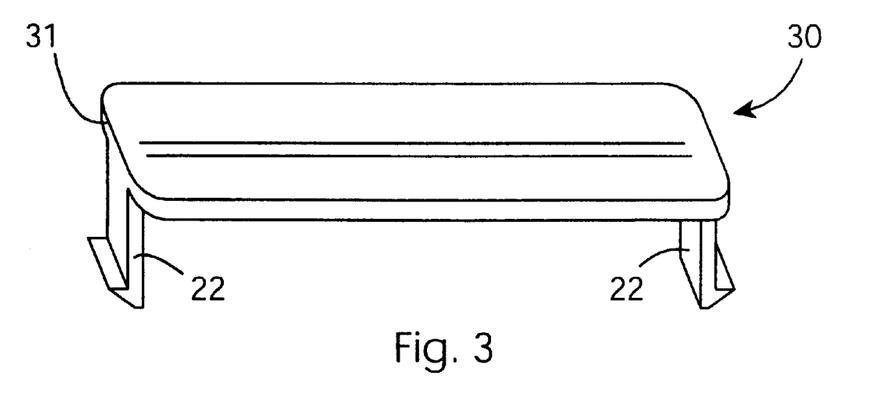
FIGS. 3 to 5 inclusive are perspective views of alternative covers.
Figure 4:
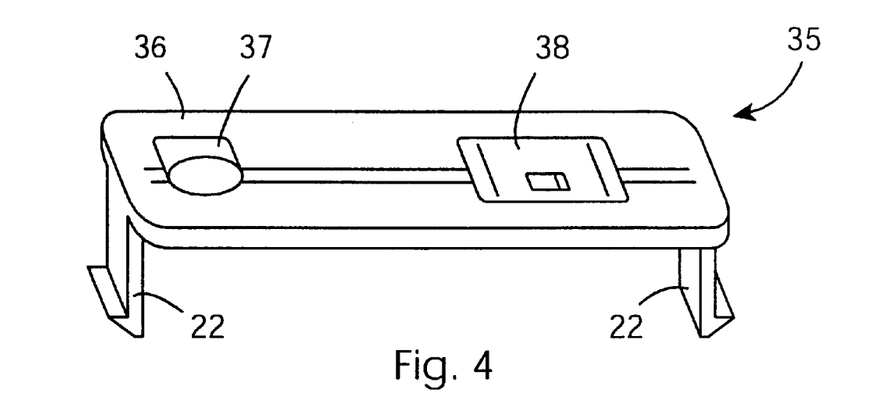
Figure 5:
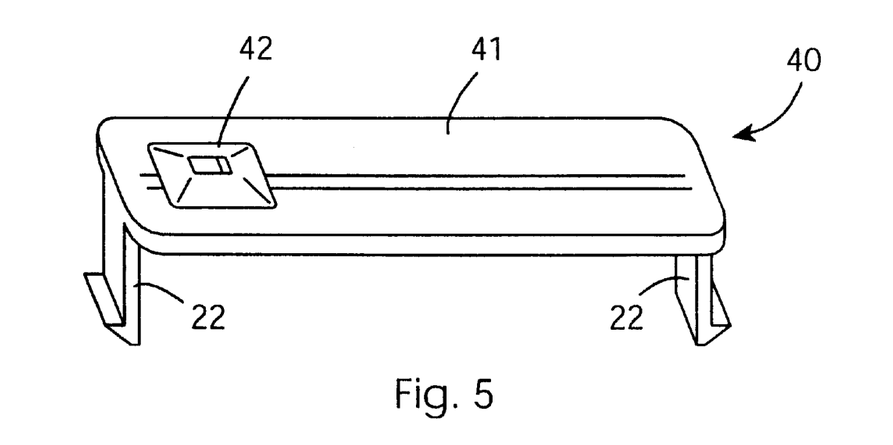

Thus, the moisture meter has a housing into which is inserted the various processing and interfacing devices. Depending on the configuration of the particular meter being produced, a cover is selected and is simply pressed into position. This allows configuration at a very late stage of production, thus providing for short lead times and production flexibility. The cover may be used as shown in FIG. 3 to only seal the housing, for example, or it may be used as shown in FIG. 4 to provide two or possibly more interfacing devices. Indeed, sensing probes may be connected to the cover according to the desired configuration. Thus, the same housing may be used for meters with different switching arrangements for example, different jack plugs, or different calibration arrangements. This also avoids the need to drill or punch a casing part.

Figure 6:
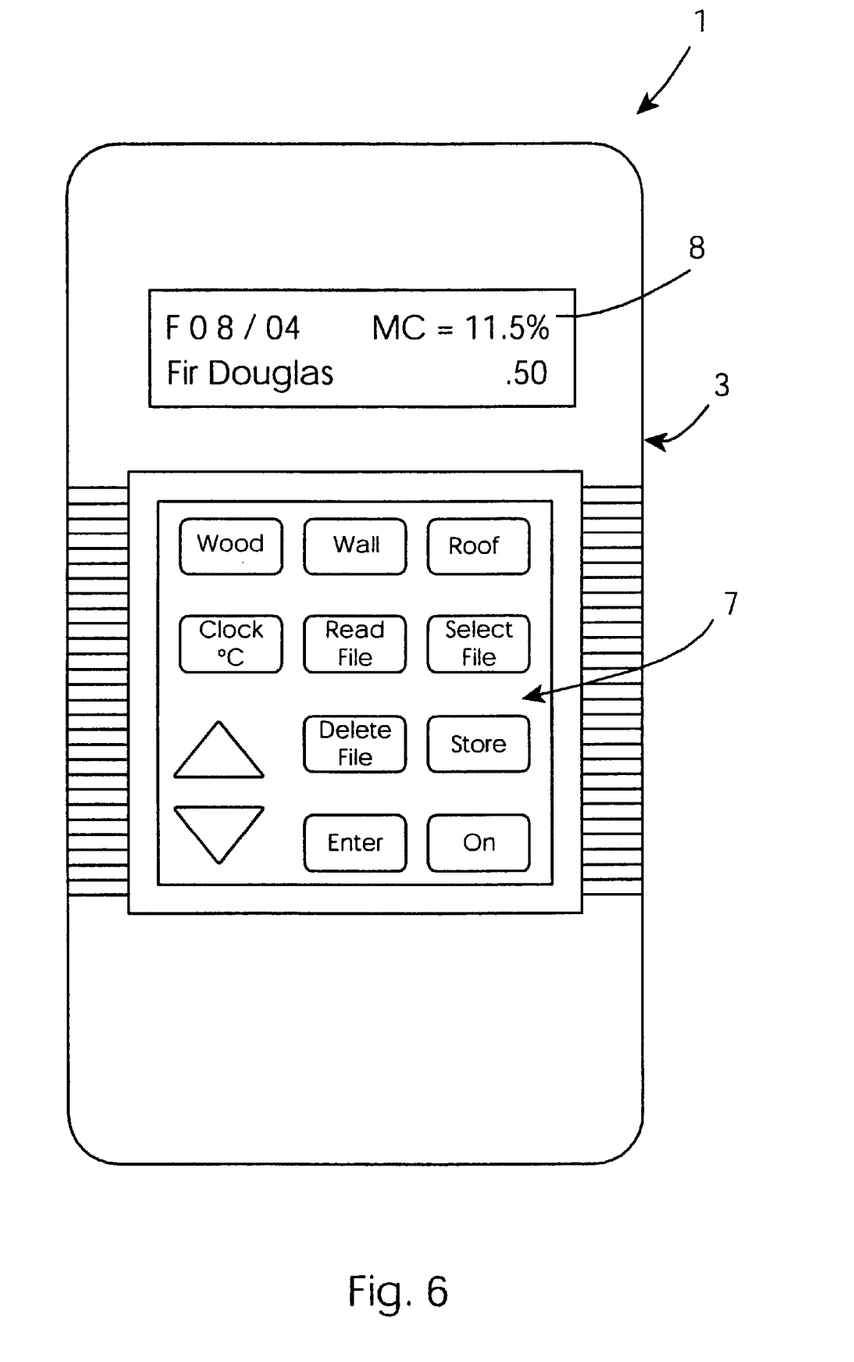
FIG. 6 is a front view of the meter showing keys of the keypad in more detail.

Referring to FIG. 6, the keypad 7 has keys dedicated to important functions to allow both selection of a mode of operation of the meter and also manipulation of data. There are keys for selection of wood, wall, and roof measurement environments. One key has dual clock and temperature functions. Other keys allow reading, selecting, deleting, and storing of files and data. Finally, there is a data entry key, an on/off switch key and up/down scroll keys.

Figure 7:
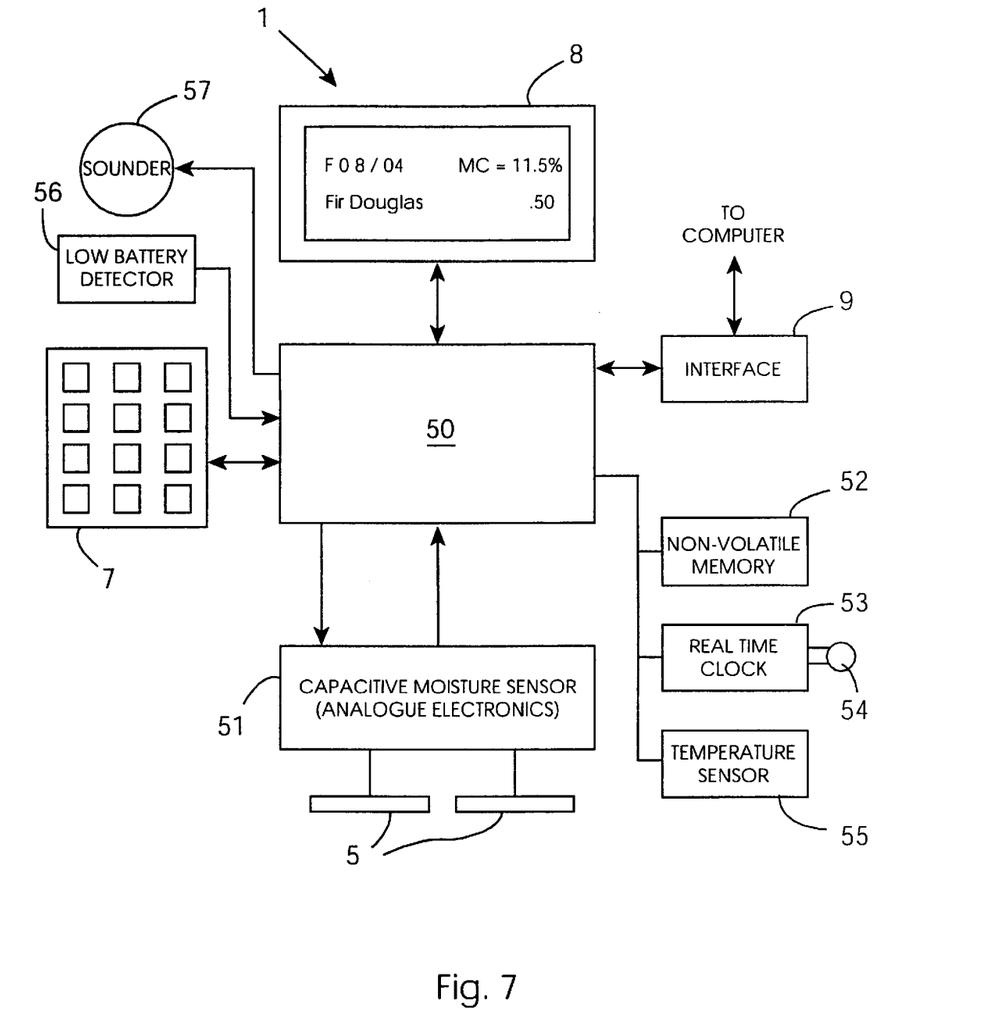
FIG. 7 is a diagram showing the architecture of the meter.

The internal architecture of the meter 1 is shown in FIG. 7. A digital microcontroller 50 performs digital data processing. The microcontroller 50 is connected to an analog drive circuit 51 for the pair of capacitive moisture-sensing electrodes 5. The meter 1 also comprises a non-volatile memory IC 52, a real time clock IC 53 with a battery backup 54 and a temperature sensor IC 55 which operate from a common 2-wire serial bus provided by the microcontroller 50. The RS232 interface 9 and a low battery detector 56 are connected to the microcontroller 50. The meter 1 is powered by a nine volt PP3 lithium manganese primary battery, not shown. Finally, a sounder 57 is also connected to the microcontroller 50.

In more detail, the microcontroller 50 is an 8-bit microcontroller having a 4096 byte program memory, an 8-bit analog to digital converter, 2 wire serial communications ($I^2C$ bus) module, USART (RS232) module, and three timer modules. The RS232 module is bidirectional, allowing download of parameter values to the meter 1.

The microcontroller 50 performs 8-bit successive approximation A/D conversion of analogue signals from the drive electronics 51. The circuit 51 comprises a 4 MHz oscillator driving a frequency divider, which in turn drives a 125 kHz square wave signal into one of the electrodes 5. The other electrode 5 is connected to a filter/amplifier/detector stage, in turn connected to a logarithmic amplifier. The filter/amplifier/detector is connected to gain switches, in turn connected to the microcontroller 50. The logarithmic amplifier delivers the analogue output to the microcontroller 50.

In more detail, in the drive circuit 51 the output from the 4 MHz ceramic resonator controlled oscillator is frequency divided by a CMOS ripple counter IC to provide a 125 KHz unity mark space square wave to drive the transmitter electrodes. An operational amplifier configured to filter, amplify and rectify the signal from the receiving electrode drives the logarithmic amplifier circuit which linearizes the exponential form of the detected signal and outputs to the microcontroller's analogue/digital converter. The gain of the filter/amplifier/detector stage is altered to suit the selected material function (wood, wall or roof) via analogue switches driven from the microcontroller 50. Further mathematical manipulation is carried out within the microcontroller 50 to correct the output of the A/D converter for the selected wood species/SG value and the temperature value from the temperature sensor 55. It also corrects for compression distortion in the drive circuits 51. The output of the temperature sensor is sampled at the same rate as the A/D converter.

The value is compared against a constant equivalent to 20° C. and the difference, plus or minus signed, is scaled and added or subtracted as appropriate to the SG/detector corrected output of the A/D converter.

This memory 52 is an 8 pin EEPROM DIL package and read/write is via the $I^2C$ two wire serial bus. Memory capacity is 64 Kilobits (8 Kbytes) which is divided into a 4 Kbit high endurance block with a 1 million (typical) erase/write capability and a 60 Kbit array with a 10,000 (typical) erase/write capability. The high endurance block is intended for frequently changed data, e.g. instrument settings. The 24LC65 has an input cache for fast write loads with a capacity of 64 bits. Data is stored in the memory 52 in records of ten fields and each field occupies 1 byte. Logs of the number of records in each file are stored in the EEPROM 52. This occupies 25 bytes, one per filelog. The EEPROM 52 also stores the wood species, wall/roof material libraries, and general meter settings.

The temperature sensor 55 is a Dallas DS1621™ serial digital temperature IC. This is an 8 pin DIL: package and operates on the 2 wire serial $I^2C$ bus along with the clock 53 and the memory 52. Temperature accuracy is 0.5° C.

The clock 53 is a Dallas DS1307™ serial real time clock IC. This device has the following features:
Counts seconds, minutes, hours, date of the month, month, day of the week, and year with leap year compensation valid up to the year 2100.
2 wire serial interface I²C.
56 byte non-volatile RAM for data storage.
Automatic power fail detect and switch circuitry.
Consumes less than 500 nA in battery back-up mode.
8 pin DIL: package.

The clock 53 requires two external components, a 32.768 kHz crystal and a small 3 volt Lithium button type back-up cell 54 to ensure that the time is maintained during main battery failure/replacement.

The meter 1 performs non-destructive moisture measurement in which the output is calculated according to:
  inputs from the sensor circuit 51 (converted to digital within the microcontroller 50),
  material parameter values such as specific gravity retrieved from memory according to a user material selection, and
  sensed temperature.

The generated data is not only displayed, but is also stored, with a capacity for 625 readings in 25 files. The data may be uploaded to PC via the socket 9, and revised parameter values may be downloaded from the PC.

Figures 8, 9:
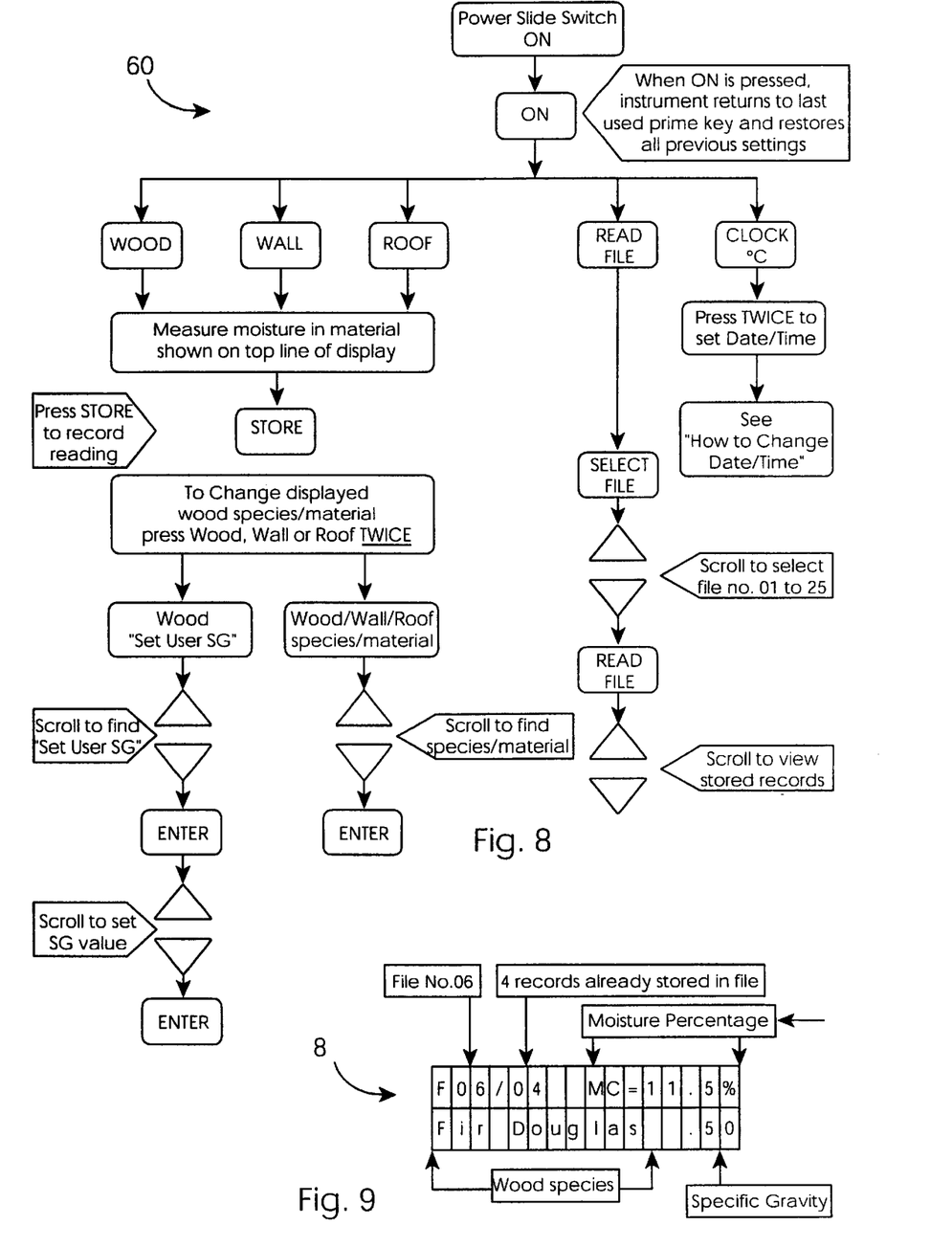
FIG. 8 is a flow diagram illustrating operation of the meter for primary key operating sequences.
FIG. 9 is a detailed view of a data display.

Referring to FIG. 8, a method 60 illustrates the main key operating sequences. The moisture data is generated for the environment selected using the Wood, Wall, or Roof keys. The particular material is named in the bottom line of the display as shown in FIG. 9, in this case "Fir Douglas". The specific gravity, in this case 0.50, is also shown. The moisture data itself is displayed on the right side of the top line, and in this case it is 11.5%. The reading may be stored by simply pressing the Store key. As shown in FIG. 9, the record is given a file number and the number of the record within the file is also indicted.

Referring again to FIG. 8, the microcontroller 50 also allows a user to change the displayed material, and the specific gravity ("SG") can be changed by use of the scroll keys. The Read File and Select File keys used together with the scroll keys allow selection and viewing of a particular record. The Clock/°C. key allows setting of the time or viewing of sensed temperature.

Figure 10:
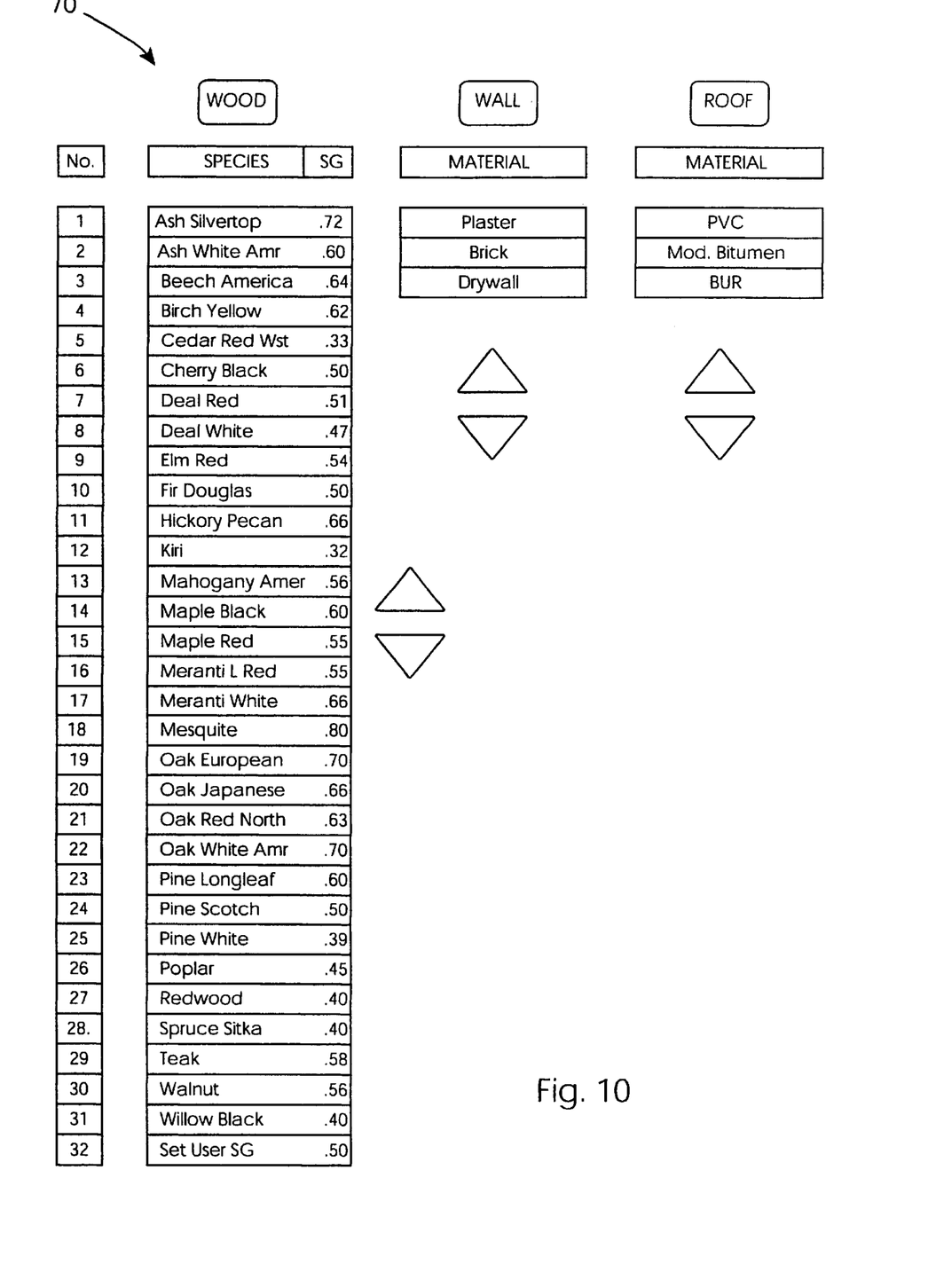
FIG. 10 is a diagram illustrating material libraries.

The microcontroller 51 uses standard libraries of data, indicated by the numeral 70 in FIG. 10. There are thirty-two species of wood, three types of wall material, and three types of roof material. The scaling factors for Wall and Roof materials are factory-set and are not accessible or visible to the user. A standard Wood library containing thirty-one selected wood species and associated specific gravity values are factory loaded together with a program for user setting of specific gravity (SG). This program ("Set User SG") permits the user to set any value between 0.30 and 0.80. Any or all of the thirty-one wood species in the meter's Wood library can be replaced via computer software which has a base library of over 300 wood species.

Figures 11, 12, 13, 14:
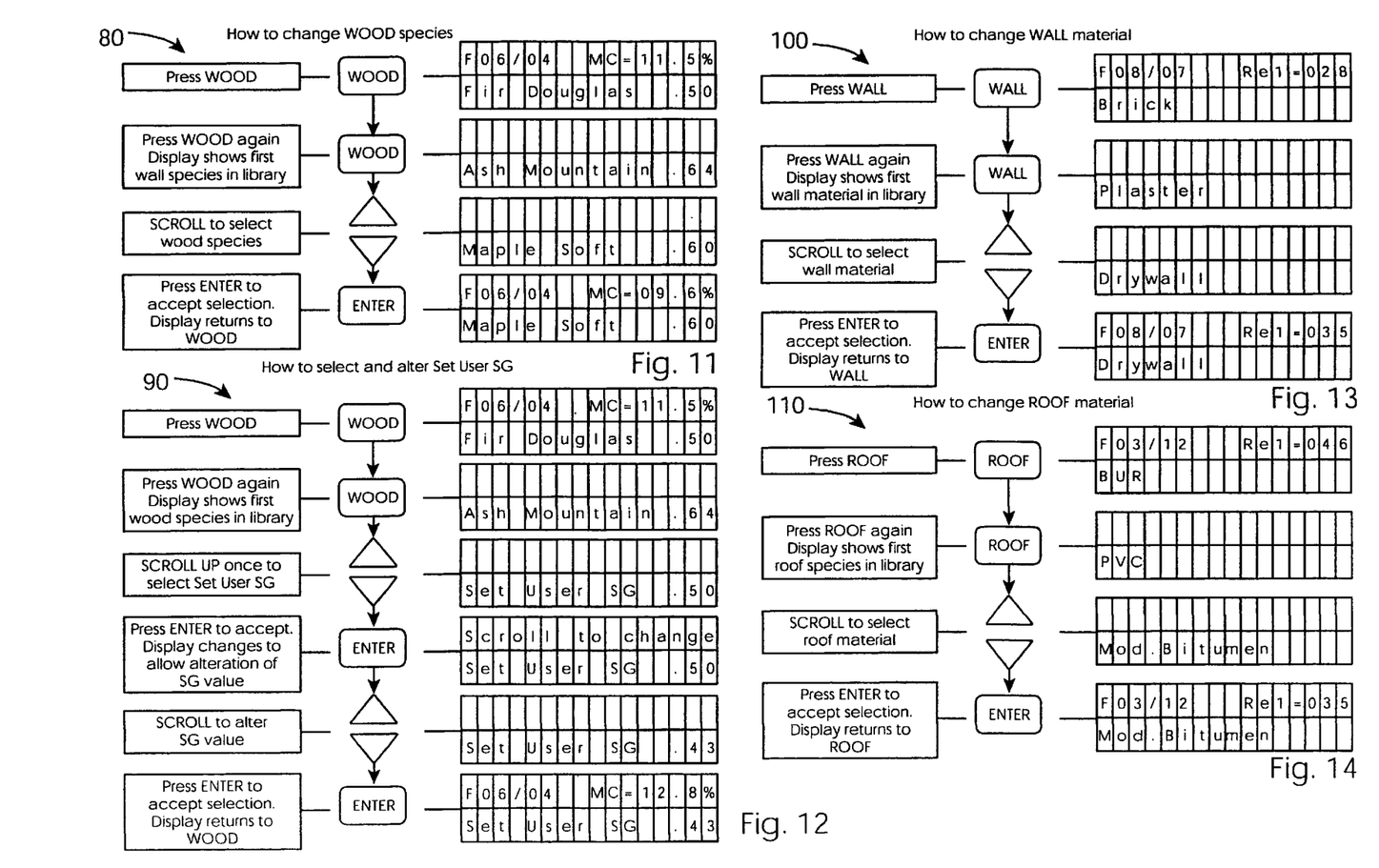
FIGS. 11 to 17 are display sequences for operations of the meter.

The drawings of FIGS. 11 to 17 illustrate how a user selects from these libraries. As shown in FIG. 11 in a sequence 80 there is default wood species, in this case Fir Douglas. A second depression of the Wood key cause the first species in the library to be displayed and the scroll keys are then used to scroll through the library. The Enter key is used to select a particular species.

Selecting and altering a specific gravity value in a sequence 90 shown in FIG. 12. A "set User SG" option is selected by scrolling up and pressing Enter. The scroll keys are then used as illustrated to alter the SG value.

A wall material is selected in a sequence 100 as illustrated in FIG. 13 using the Wall, scroll, and Enter keys. Roof material is selected likewise, in a sequence 110 illustrated in FIG. 14.

Figure 15:
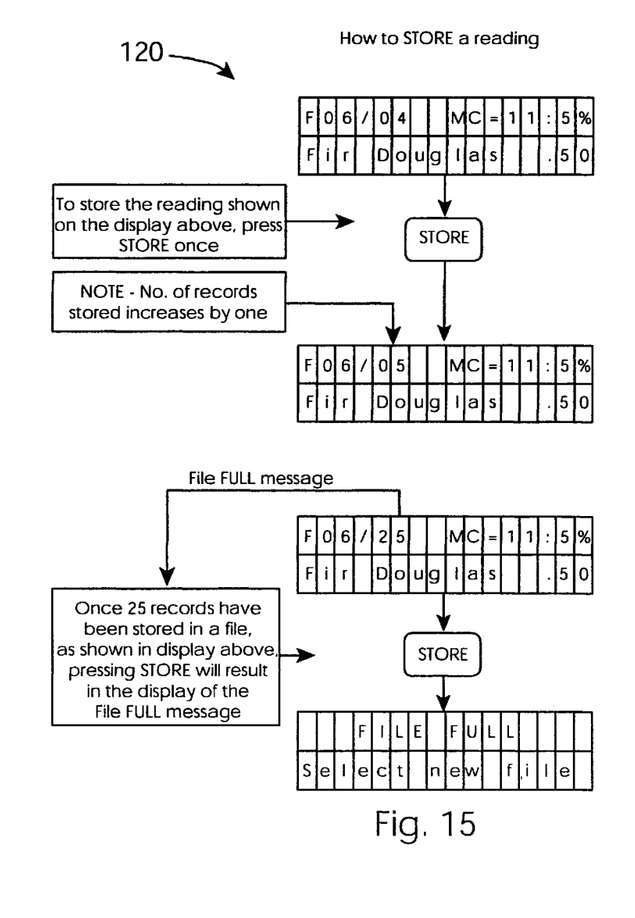
Figure 16:
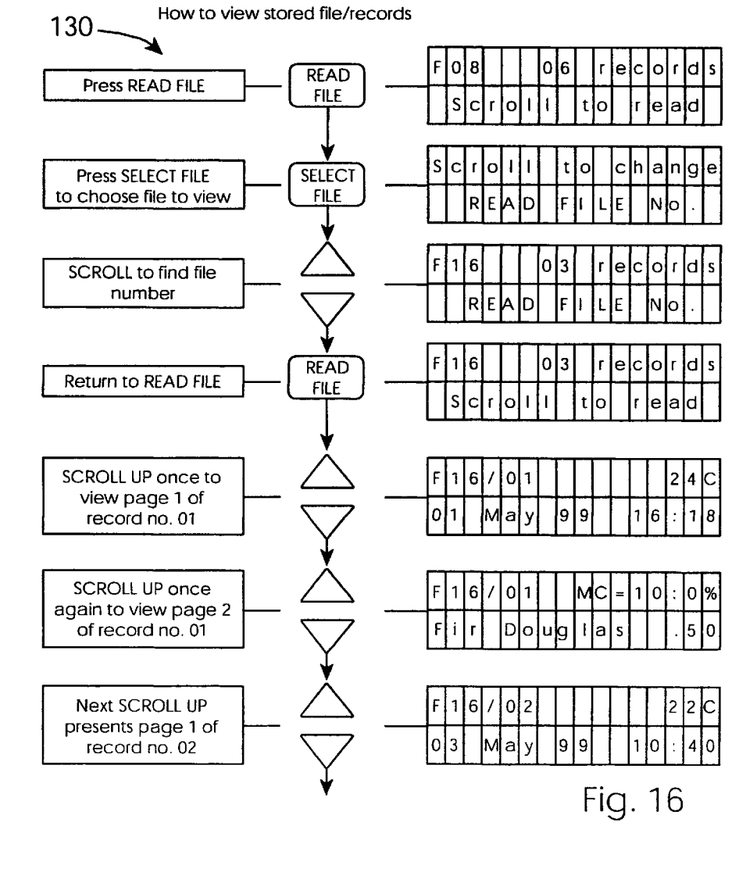
Figure 17:
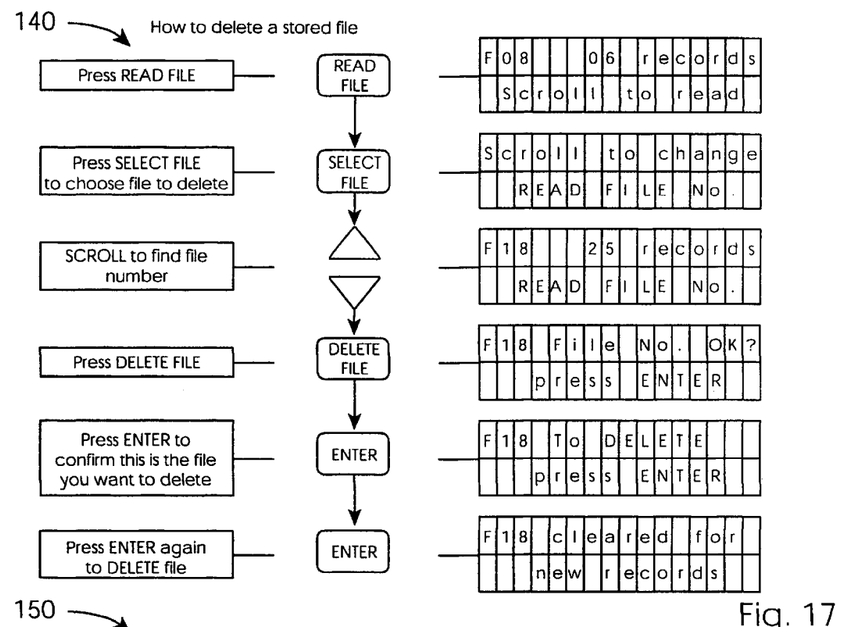

A sample display for a particular reading is shown at the beginning of FIG. 15. To store, the Store key is pressed and the record number for the file is incremented. If the fill is full (25 records), the user is prompted to select a new file. As shown in FIG. 16 the Read File, Select File, scroll, and Read File, keys are used to read selected records in selected files in a sequence 130. As shown in this drawing, each record comprises a first "page" indicating the temperature, data, and time of the reading, and the second "page" indicates the moisture percentage, material, and specific gravity. Thus a surveyor can recall a large number of readings at the end of a survey or surveying period. The date, time, and material data help to identify the location of the reading. The surveyor can use particular files for particular surveys or parts of surveys in a manner which suits him or her. File and record management is also performed by deleting files, as illustrated in a sequence 140 shown in FIG. 17. In this embodiment, it is not possible to delete individual records, only full files. The Delete File action clears all 25 files in the relevant file.

Figure 18:
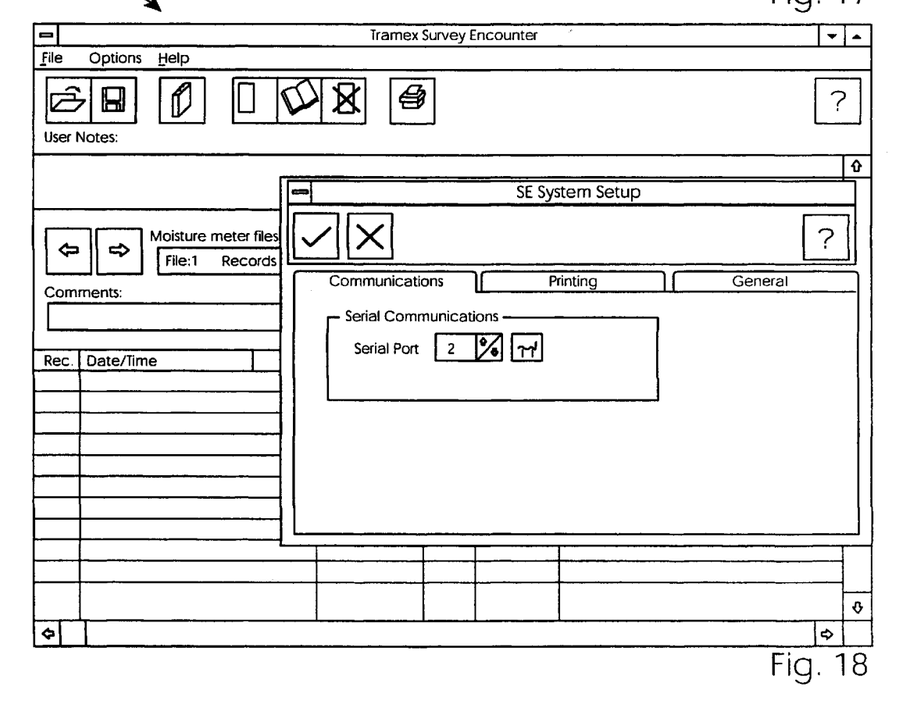
FIG. 18 is a sample screen display for a computer interfacing with the meter.

The meter 1 may be connected to a computer by an RS232 link to the socket 9. A PC setup screen 150 is shown in FIG. 18. This allows selection of the communication port and other technical parameters.

After the setup is complete, selected records may be uploaded and software on the PC allows users to annotate at any one of three levels as follows.

1. User Notes

In a User Notes box one can type up to 32000 characters of description, comments, remarks, etc., applicable to the complete download. When printed this appears at the end of the report.

2. Files Notes

In the Comment box located on the middle bar ("Moisture meter files") one can type up to 250 characters of notes/comment on each file. It is not possible to type file notes if there are no records in the file.

3. Record Notes

In a Notes column of the spreadsheet display of individual records one can type up to 120 characters of notes/comment against each record. One can double click on the selected line and type notes in the drop down box. It is not possible to type notes if there is no record on that line.

The downloaded data complete with any notes that have been added can be saved to the PC hard drive disc or a floppy disc by clicking on the File menu (to the left on the top bar) and selecting Save. This will open the normal Windows™ Save As dialog box. The user can type in a file name, select a drive letter (to save to a floppy disc) and click the OK button. The file will then be saved under the inputted filename and with the file extension MEX added.

Loading a previously saved download file is possible by selecting Open or by clicking on the "Open file" button on the toolbar. The normal Windows™ Open dialog box will appear and the user selects the file to view.

One can set printing margins and change the font by using the Options/SE System Setup/Printing menu. If one clicks the Print button on the top toolbar a Print control box will appear. This allows one to change the printer, provides the options of printing the entire download data or only the records file displayed in the main window and an OK button to click when you are ready to print.

The saved data may be copied using Windows™ Clipboard facility to other applications, such as those of the Microsoft Office suite for more detailed analysis and/or to enable reports with the actual readings to be compiled.

The PC software also provides an Edit Library facility containing a database of over 300 wood species and their associated specific gravity values. A meter's library can be downloaded to a PC and viewed in a double list presentation with the PC database library. The meter's library can be simply edited by using Add/Remove buttons. When uploading a new library to a meter the software must first erase any data records in the meter. This is necessary because the old data refers to the previous library and would be corrupted if it attempted to use the new library. It is therefore most important to save the old data before loading a new library. The software presents a warning message regarding these matters and automatically saves the data records into a backup file before uploading a new library.

It will be appreciated that the invention provides for measurement of moisture is a very versatile manner because of the range of parameters in the library. It also achieves excellent accuracy because of the availability of material parameters and because of the automatic temperature compensation and the data processing correction operations generally. Another major advantage is the fact that the data may be stored and manipulated either in the meter only or and/or in a PC. Also, the housing constitution allows configuration of the meter in a very simple manner at a late stage in the production process. The top opening allows access for such things as setting calibration values before the housing is finally sealed for the appropriate interfacing required.

The invention is not limited to the embodiments described but may be varied in construction and detail within the scope of the claims.

What is claimed is:

1. A moisture meter comprising:

a hand-held housing supporting a moisture sensor for contact with a material being surveyed, an output interface, and a controller including means for determining moisture content data according to signals from a moisture sensor drive circuit and for outputting said data to an output interface, the meter including a user input interface, a non-volatile memory, and means in the controller for storing a library of parameter values of a plurality of materials, said values each including a material specific gravity value, the controller including means for selecting stored material parameter values from said library in response to user inputs, the controller including means for performing data processing with said selected parameter values to determine a moisture content value of a material in contact with the moisture sensor, said data processing means including means for compensating signals received from the moisture sensor drive circuit according to said specific gravity of said material, the controller including means for storing a plurality of data records in said non-volatile memory, each said record including data indicating a material type, date of a reading, and said moisture content value, the meter includes an interface for communicating with a host computer, and the controller including means for receiving an updated library of material values from a host computer via said interface and for storing said library in said non-volatile memory, and means for uploading said stored data records to a host computer via said interface.

2. The moisture meter as claimed in claim 1, wherein the controller comprises an analog to digital converter for conversion of analog signals from the moisture sensor drive circuit.

3. The moisture meter as claimed in claim 2, wherein the controller comprises means for setting gain values for the moisture sensor drive circuit according to the selected material parameter values.

4. The moisture meter as claimed in claim 2, wherein the controller comprises means for setting gain values according to the selected material parameter values by setting gain switches connected to a filter/amplifier/detector stage of the moisture sensor drive circuit.

5. The moisture meter as claimed in claim 2, wherein the controller comprises means for setting gain values according to the selected material parameter values by setting gain switches connected to a filter/amplifier/detector stage of the moisture sensor drive circuit, and wherein the filter/amplifier/detector stage is connected to a logarithmic amplifier having means for linearizing the exponential form of a signal from said stage and providing an output signal to the controller.

6. The moisture meter as claimed in claim 1, wherein the meter further comprises a temperature sensor and the controller includes means for performing compensation according to a sensed temperature value.

7. The moisture meter as claimed in claim 6, wherein the controller comprises an analogue to digital converter, and means for correcting the output of said converter according to sensed temperature.

8. The moisture meter as claimed in claim 1, wherein the input interface comprises a key dedicated to each of a plurality of material type groups.

9. The moisture meter as claimed in claim 1, wherein the input interface comprises a key dedicated to each of a plurality of material type groups and the groups include wood, wall, and roof material types.

10. The moisture meter as claimed in claim 1, wherein the input interface comprises a scroll key and the controller includes means for scrolling through library items in response to said scroll key.

11. The moisture meter as claimed in claim 1, wherein the controller comprises means for storing each data record within one of plurality of files.

12. The moisture meter as claimed in claim 1, wherein the controller comprises means for automatically writing a temperature value for a moisture content reading to an associated data record.

13. The moisture meter as claimed in claim 1, wherein the meter housing comprises a non-removable cover adjacent to a side edge of a circuit board contained within the housing.

14. The moisture meter as claimed in claim 13, wherein the cover has an aperture for access to an interfacing device of the meter.

15. The moisture meter as claimed in claim 13, wherein the cover is in a top side of the meter housing.

16. The moisture meter as claimed in claim 13, wherein the cover comprises a pair of opposed snap-fitting tabs engaging behind corresponding receivers in housing main body.

17. The moisture meter as claimed in claim 1, wherein the controller comprises means for allowing a user to adjust a specific gravity value of a material.

18. The moisture meter as claimed in claim 1, wherein the controller comprises means for storing user-inputted text notes associated with data records.

19. The moisture meter as claimed in claim 1, wherein the controller comprises means for storing user-inputted text notes in a notes record associated with all data records, a notes record associated with a file of data records, and a notes record associated with an individual data record.

20. A computer readable medium comprising:

software code for directing a host computer, said host computer for downloading parameter values to a moisture meter and for receiving moisture content data from said moisture meter, said moisture meter including a hand-held housing supporting a moisture sensor for contact with a material being surveyed, an output interface, and a controller including means for determining moisture content data according to signals from a moisture sensor drive circuit and for outputting said data to an output interface, the meter includes a user input interface, a non-volatile memory, and means in the controller for storing a library of parameter values of a plurality of materials, said values each including a material specific gravity value, the controller includes means for selecting stored material parameter values from said library in response to user inputs, and means for performing data processing with said selected parameter values to determine a moisture content value of a material in contact with the moisture sensor, said data processing means includes means for compensating signals received from the moisture sensor drive circuit according to said specific gravity of said material, the controller includes means for storing a plurality of data records in said non-volatile memory, each said record includes data indicating a material type, date of a reading, and said moisture content value, the meter includes an interface for communicating with a host computer, and the controller includes means for receiving an updated library of material values from a host computer via said interface and for storing said library in said non-volatile memory, and means for uploading said stored data records to a host computer via said interface.

21. A moisture meter comprising:

a hand-held housing supporting a moisture sensor for contact with a material being surveyed, an output interface, and a controller having means for determining moisture content data according to signals from a moisture sensor drive circuit and for outputting said data at the output interface, the meter includes a user input interface, a non-volatile memory, and means in the controller for storing a library of parameter values of a plurality of materials, said values each including a material specific gravity value, the controller including means for selecting stored material parameter values from said library in response to user inputs, the controller including means for performing data processing with said selected parameter values to determine a moisture content value of a material in contact with the moisture sensor, said data processing means having means for compensating signals received from the moisture sensor drive circuit according to said specific gravity value of said material, the controller including means for storing a plurality of data records in said non-volatile memory, each said record including data indicating a material type, date of a reading, and said moisture content value, the meter having an interface for communicating with a host computer, the controller having means for receiving an updated library of material values from the host computer via said interface and for storing said library in said non-volatile memory, means for uploading said stored data records to a host computer via said interface, and means for setting gain values according to the selected material parameter values by setting gain switches connected to a filter/amplifier/detector stage of the moisture sensor drive circuit, and a logarithmic amplifier having means for linearizing the exponential form of a signal connected to the filter/amplifier/detector stage from said stage and providing an output signal to the controller.

* * * * *